(12) United States Patent
Uram

(10) Patent No.: US 6,997,868 B1
(45) Date of Patent: Feb. 14, 2006

(54) AUTOCLAVABLE ENDOSCOPE

(76) Inventor: Martin Uram, 39 Sycamore Ave., Little Silver, NJ (US) 07739

( * ) Notice: Subject to any disclaimer, the term of this patent is extended or adjusted under 35 U.S.C. 154(b) by 29 days.

(21) Appl. No.: 10/901,252

(22) Filed: Jul. 27, 2004

(51) Int. Cl.
*A61B 1/04* (2006.01)

(52) U.S. Cl. ...................................... 600/133; 600/129

(58) Field of Classification Search ................ 600/129, 600/133
See application file for complete search history.

(56) References Cited

U.S. PATENT DOCUMENTS

| | | | | |
|---|---|---|---|---|
| 5,121,740 | A | * | 6/1992 | Uram .......................... 600/108 |
| 5,443,057 | A | * | 8/1995 | Elmore ........................ 600/133 |
| 5,810,713 | A | * | 9/1998 | Rondeau et al. ............ 600/133 |
| 6,572,536 | B1 | * | 6/2003 | Bon et al. .................... 600/133 |

* cited by examiner

*Primary Examiner*—Beverly M. Flanagan
*Assistant Examiner*—Matthew Kasztejna
(74) *Attorney, Agent, or Firm*—Reed Smith, LLP

(57) ABSTRACT

An autoclavable endoscope, such as the type used in ophthalmological operations, has a probe that contains optical fiber guides such as an image guide, a laser guide and an illumination guide. The distal end of these guides are sealed to the distal end of the probe with a high temperature medical grade epoxy. The epoxy is selected to retain its structural and optical properties at autoclaving conditions. A preshrunk flexible plastic jacket extends proximal of the handle around the three guides. Because it is preshrunk at autoclavable temperatures, it is not further damaged during autoclaving. The epoxies used proximal to the probe have to be high temperature epoxies but are generally preferably a more flexible urethane type epoxy. Proximal connectors and ferule for the guides are selected metals to retain size and/or conduct heat.

12 Claims, 2 Drawing Sheets

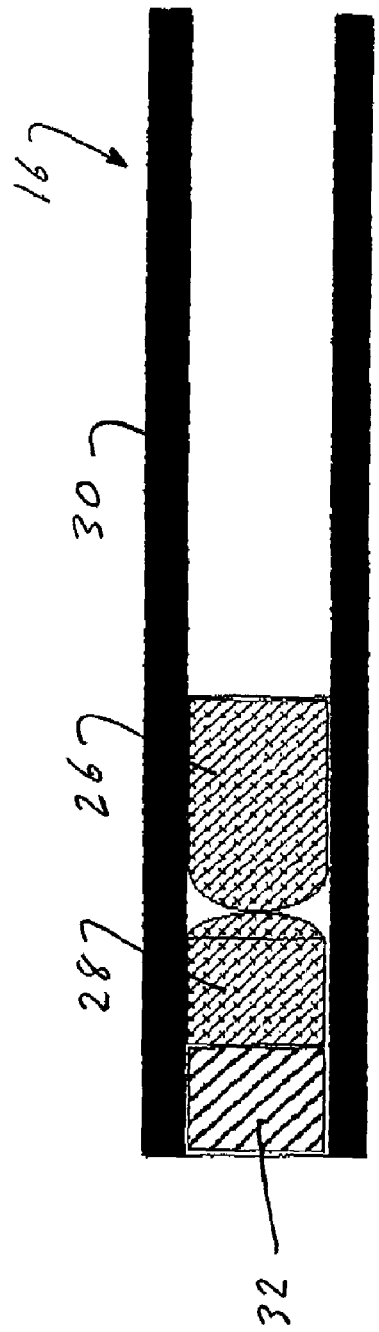
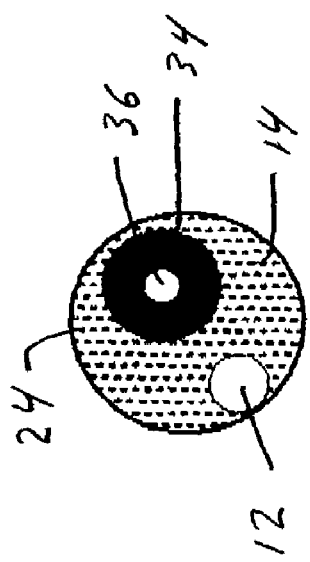

AUTOCLAVABLE ENDOSCOPE

BACKGROUND OF THE INVENTION

This invention relates in general to a design that makes possible the autoclaving of a fiberoptic endoscope used for medical purposes.

One application of this invention is to an endoscope used in certain ophthalmologic operations. The disclosure herein relates to that embodiment.

As shown, for example, in Applicant's U.S. Pat. No. 5,121,740 issued Jun. 16, 1992, it is known to provide an endoscope which may contain an optical fiber illumination guide, an optical fiber laser guide and an optical fiber image guide to perform surgical operations in various parts of the eye.

It is important that such an endoscope, as well as other types of endoscopes used for other surgical operations, be sterilized between each use or, if that cannot be satisfactorily done, disposed of after first use.

In some venues, it is acceptable to employ a high level disinfectant after the use of the endoscope so that it can be reused. In other venues, only the autoclaving under known high temperature steam conditions is acceptable.

An endoscope such as the type described in U.S. Pat. No. 5,121,740 cannot be autoclaved and reused. Essentially, when autoclaved, the known endoscopes tend to lose their critical optical characteristics and do not provide the clear and focused image that is required for a surgical operation.

Accordingly, it is a primary purpose of this invention to provide an endoscope design which can be autoclaved so that the endoscope can be reused.

It is a further object of this invention that this autoclavable endoscope be provided at a cost which makes it cost effective to use compared to the presently available non-autoclavable endoscopes.

It is a related purpose of this invention to provide an autoclavable endoscope with a configuration and utility that sufficiently resembles that of the prior art non-autoclavable endoscopes so that its use will be familiar and comfortable for the surgeon or physician.

BRIEF DESCRIPTION

In brief, in the embodiment of this invention disclosed herein, a known type of a three optical guide endoscope is provided in which there is a laser fiber guide, an illuminating fiber guide and an image fiber guide.

These three light guides are attached at proximal ends, to respectively a laser connector, a xenon light source connector and a camera connector.

The three optical guides attached to these connectors are brought together into a single flexible jacket. At the distal end of the jacket, they are brought through a hand piece to a probe, which probe is a stainless steel cylinder. This cylinder is effectively a hypodermic needle having an outer diameter of, for example, 960 microns (0.96 mm).

Autoclaving is at 265 degrees F. for 15 minutes. The features that make this design autoclavable are as follows:

The epoxies used at the distal end to seal all three optical systems to the stainless steel probe and to seal the protective window and lens of the system within the distal end of the image guide are high temperature resistant, medical grade epoxies.

It is particularly important that the specific epoxy used on the lens which is focused is one that can be cured in a relatively short period of time (15 to 30 minutes) so that the focus established can be permanently set. Since the lens to be focused is proximal of the window and companion lens, that epoxy need not be medical grade.

A third feature is in the use of a preshrunk thermoplastic elastomer jacket material to enclose the three optical systems throughout the flexible zone proximal of the hand piece. The preshrinking of this material minimizes its dimensional change during autoclaving. The term preshrunk herein refers to preshrinking at high temperature.

A fourth feature relates to an appropriate construction of the connector at the proximal end of the light fiber. The light fiber portion of the light guide is sealed to a copper ferule with a high temperature epoxy that retains its structure under high temperature to minimize injury of the fragile light fiber system, which injury occurs if the epoxy melts or runs. The material of the ferule is copper so as to dissipate the heat from the xenon light source. This will further serve to minimize injury to the fragile light fiber system. The copper ferule is within an aluminum connector.

The camera connector, which in the prior art is a plastic material, is replaced by anodized aluminum. This avoids swelling during autoclaving. It is a necessary change to make sure that after autoclaving the connector will couple into the socket of a camera.

In addition, all epoxies used are high temperature resistant to withstand the 15 minutes at 265° F. autoclaving regimen.

BRIEF DESCRIPTION OF THE FIGURES

FIG. 2 is a longitudinal sectional view through the image cannula 30 at the distal end of the endoscope. FIG. 2 is at a much greater scale than that of FIG. 1.

FIG. 3 is a cross-sectional view through the probe 24 at the juncture between the quartz window 32 and the lens 28. FIG. 3 illustrates the reticule 34 that creates the aperture step 36.

DESCRIPTION OF THE PREFERRED EMBODIMENTS

Figure 1:
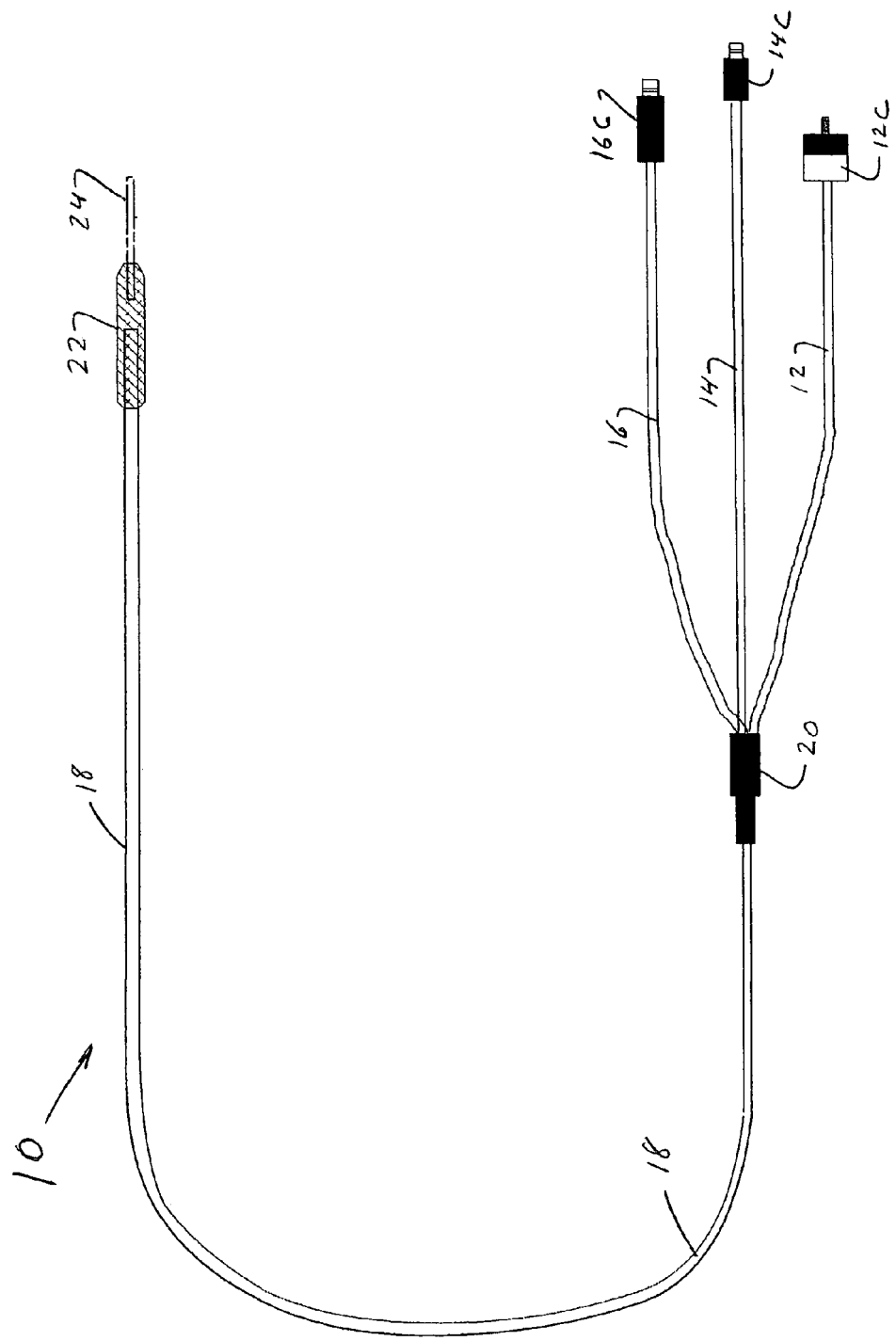
FIG. 1 is a schematic illustration of the endoscope extending from distal probe 10 to proximal connectors 12C, 14C, 16C.

The FIGs. illustrate a single embodiment. This endoscope 10 has three main optical guides. They are a laser fiber guide 12, a set of fibers to provide a light guide 14 and an image guide 16 having approximately 10,000 light elements to provide 10,000 pixels. These three optical guides 12, 14 and 16 are held in a plastic jacket 18. This jacket 18 extends from a trifurcation zone 20 to the hand piece 22 near the distal end of the endoscope 10.

Distal of the hand piece 22 is the stainless steel cylindrical probe 24. The three light guides 12, 14, 16 extend through the probe 24 and are flush with the distal end of the probe 24.

Proximal of the trifurcation zone 20, the three optical guides are in three separate jackets extending to appropriate connectors 12C, 14C, 16C of the optical systems to a laser, a light source and a camera, respectively.

Specifically, connector 12C at the distal end of the laser fiber guide 12 permits coupling to a laser. A connector 14C at the proximal end of the light fiber guide 14 permits connecting to a xenon light source and a connector 16C at the distal end of the image guide 16 permits connection to a camera.

The fibers of the laser fiber guide 12 and light fiber guide 14 extend flush to the distal end of the probe. However, the fibers of the image guide 16 extends to the point where they contact the compound lens that consists of a first lens element 26 and a second lens element 28 (see FIG. 2).

One of the features that makes an endoscope not autoclavable is that steam enters around and between the two lenses 26, 28 thereby changing the optical properties and degrading the image involved. Therefore, it becomes important that particular attention be made to the design at the distal end of the image guide 16.

A thin wall stainless steel cannula 30 surrounds and supports the distal end of fibers of the image guide 16. At the distal end of this cannula 30, is a transparent protective quartz window 32. The window 32 is immediately distal of the two lenses 26 and 28. The lens 26 is epoxy bonded to the distal end of the fibers of the image guide 16. The spacing between the lenses 26 and 28, as well as the spacing between the lens 28 and the window 32 are only enough to prevent chromatic aberration. The lens 28 and the window 32 are sealed along their peripheries to the cannula 30 by a high temperature resistant epoxy. FIG. 3 illustrates the reticule 34 that creates the aperture stop 36 for the image that is to be collimated by the lens system 26, 28.

FIG. 3 shows the light fiber bundle in a geometric state which is distal of the hand piece 22. Proximal of the hand piece, the light fiber bundle is a more coherent bundle with a circular cross-section having its own separate geometry and is within its own jacket. But in order to achieve as small a probe as possible, it is more efficient for the light bundle to be distributed in the fashion shown in FIG. 3.

The autoclavable endoscope 10 of this invention is made possible by a selection and treatment of materials which in combination permit autoclaving without deterioration of operating characteristics. It should be understood that the endoscope of this invention is not indefinitely autoclavable. That is, after it has been autoclaved a number of times (for example, a dozen times), its operating characteristic may degrade and can no longer be used. The key characteristics that normally degrade initially are the focus or clarity of the image provided by the image guide 16 and/or the loss of light due to the breakdown of epoxy at the connector 14C for the light guide.

Applicant believes that the invention involved herein is primarily in the selection of materials (and importantly, the particular epoxies) that are subjected to an autoclaving temperature of 265 degrees F., a temperature which is close to the temperature limit at which these epoxy materials retain their sealing and transparency characteristics.

With this invention, it becomes possible, at reasonable cost and without material change in the manner of operation of the endoscope, to provide a device which can be autoclaved a number of times.

In large part, this invention is a trade-off between: (a) maintaining reasonable cost, (b) providing an autoclavable endoscope, and (c) providing an endoscope that operates substantially in the same fashion as do comparable endoscopes known to the profession.

As part of this trade-off, that there is an economic trade-off between: (a) the cost of the non-autoclavable endoscope, (b) the cost of the autoclavable endoscope of this invention and (c) the number of times at which the endoscope of this invention can be autoclaved. Applicant believes that this invention provides a combination which optimizes these trade-offs.

A significant epoxy is the one employed at the distal end of the probe 24 to seal in the three light guides 12, 14 and 16 and also to seal the distal lens element 28 and quartz window 32 to the cannula 30. It is a high temperature resistant, overnight setting, medical grade epoxy. This high temperature resistance requires both that it not melt during the autoclaving process and that it retain a substantial transparent characteristic before and after autoclaving. An epoxy has been identified which maintains its color and geometry when subjected to the autoclaving process. This epoxy, when subject to autoclaving, is effectively pushed to its limit. Applicant believes this is a reason why this autoclavable endoscope can only be autoclaved a limited number of times; for example, twelve to fifteen times, before losing its image definition and clarity.

A second epoxy seals the proximal lens element 26 to the cannula 30. It is a high temperature epoxy which has a faster setting time than does the epoxy used for sealing the three light guides to the probe 24. It sets in 15 to 20 minutes at 166 degrees F. It also maintains its geometry and optical transparency during autoclaving. It need not be medical grade.

Both of the above epoxies are selected for the optical characteristic that they are not black and are transparent or amber and maintain this optical characteristic after autoclaving. The transparency of the epoxy is important to assure non-interference with the transmission of light.

By contrast, the epoxy at the trifurcation 20 and proximal end of the three systems is generally preferably a more flexible epoxy such as a urethane. The urethane can be black in color and need not be medical grade. However, such epoxy must withstand the autoclaving temperature and time.

A further feature is that the thermoplastic elastomer jacket 18 is pre-shrunk at autoclaving temperature to prevent it from being damaged during autoclaving.

It is further important that the prior art plastic connector 16C to the camera is replaced by anodized aluminum to prevent swelling during autoclaving so that it can be reused and will fit into the camera socket. The epoxy used to bond the image guide fibers and ferule to the aluminum connector 16C is not as critical as some of the other epoxies and may be a standard epoxy.

Another important feature is that the ferule within the connector 14C for the light guide be of copper so as to dissipate the heat from the xenon light source. The connector 14C shell is aluminum. A high temperature epoxy such as that used to bond the lens 26 to the cannula 30 is used to bond the light fibers to the ferule. The copper ferule and epoxy used at the ferule minimize damage to the delicate fibers used for this illumination guide.

In particular, in one embodiment of the invention, the probe 24 is a 33 mm long stainless steel cylinder with an OD of 960 microns and an ID of 880 microns. The stainless steel cannula 30 is a 24 gauge cylinder having a 570 micron (0.57 mm) outside diameter, a 520 micron inside diameter and a length of 331 microns. Within the cannula 30, there is the two element 26, 28 compound lens and the transparent quartz window 32. The quartz window 32 is 250 microns long, the lens element 26 is about 590 microns and the lens element 28 is approximately 370 microns. The three elements 26, 28 and 32 are longitudinally spaced from one another only enough to avoid chromatic aberration. Thus, the spacing is in the range of a fraction of a micron. The fiber optic bundle for the image system 16 extends through into cannula 30 and is bonded to the proximal surface of the lens element 26. The surface of the quartz window 32 is essentially flush with the end of the cannula 30 and the end of the probe 24. The lens elements 26 and 28 as well as the window 32 are held in place by a full circular epoxy band. This epoxy band extends over about the proximal 150 microns portion of the window 32 and also over about 250 microns of the distal portion of the lens element 28. This full circular epoxy band which binds the elements 28 and 32 to the inner surface of the cannula 30 wall serves to prevent steam under the pressures and temperatures of autoclaving from getting into the spaces between the lens and window elements 26, 28 and 32.

In one embodiment that has been tested, the following have been successfully employed.

A first epoxy that is used to bond the guides 12, 14 and 16 to the probe 24 is a Master Bond 42HT MED available from Master Bond, Inc. of 154 Hobart Street, Hackensack, N.J. 07601. This epoxy sets over night in approximately twelve hours at room temperature. This epoxy is also used to bond the lens 28 and window 32 to the cannula 30.

In fabrication, the lens 26 is used to establish the focus. Thus the epoxy that bonds the lens 26 to the cannula 30 has to be one that sets more quickly than does the 42HT MED. The epoxy used is an EPOTEK 353ND-T epoxy available from Epoxy Technology. Inc. at 14 Fortune Drive, Billerica, Mass. 01821. Under a heat lamp at 166° F., it cures in between 15 to 20 minutes. This provides a useful setting time within which to establish the focus and obtain a permanent set.

Both of the above epoxies have properties which allow them to withstand 265° F. for 15 minutes for a limited number of times without significantly changing their structural and light transparency properties.

Another area where the selection of epoxies has to be carefully chosen is at the connector end of the endoscope. A Master Bond 43HT Medical epoxy can be used to bond the laser guide 12 fiber to the laser connector 12C as well as to bond the light guide 14 fiber to a ferule that is in the connector 14C. In the latter case, for convenience in terms of available oven, applicant has also used the EPOTEK 353 ND-T.

The high temperature created by the laser at the laser connector 12C and by the xenon light source at the light guide connector 14C requires the use of epoxies that withstand not only the autoclaving temperature but the temperature from the light sources when the endoscope is in use.

A HYSOL 608 standard epoxy has been used at the image guide to bond the image fiber to a ferule which in turn is bonded to the connector 16C. This epoxy primarily has to be able to withstand the autoclaving temperature without substantial physical distortion. It is available from Loctite Corp. in Rocky Hill, Conn. 06067.

At other locations, such as when bonding the ferule to the light guide connector 14C and the ferule to the image guide connector 16C, the jackets of the guides of all three connectors, bonding at the trifurcation 20 and bonding of the jacket to the hand piece 22, a double bubble urethane epoxy D85 has been used. It is available from Elements Specialties, Inc. of Belleville, N.J. 07109. It has the advantages of bonding well to plastic and not melting at the autoclaving temperatures.

While the foregoing description and drawings represent the presently preferred embodiments of the invention, it should be understood that those skilled in the art will be able to make changes and modifications to those embodiments without departing from the teachings of the invention and the scope of the claims.

For example, the invention has been described in connection with an endoscope having three different fiberoptic systems. Yet, it could be employed with an endoscope having the illumination guide and image guide without the laser guide.

What is claimed is:

1. In an autoclavable endoscope having a probe with a sidewall containing at least an optical fiber illumination guide having light fibers, a laser fiber guide and an optical fiber image guide and wherein the distal end of the image guide contains a cylindrical cannula within which is positioned a window at the distal end of the cannula, an objective lens having first and second lens elements proximal to and adjacent to the window, the image guide fibers being proximal and adjacent to the proximal one of the lens elements, and a handle proximal to the probe, the improvement comprising:

a preshrunk flexible plastic jacket extending proximal of the handle and encompassing said optical guides, a trifurcation zone at the proximal end of said jacket from which zone said guides extend proximally, a first type epoxy bonding the distal ends of said guides to said probe, said first epoxy also bonding the circumference of the distal lens element and the circumference of the window within the cylindrical cannula at the end of the image guide, a second type epoxy bonding the proximal lens element to the cannula, a third type epoxy bonding said jacket to the optical guides at said trifurcation, said first type epoxy being a medical grade, high temperature resistant, overnight setting epoxy which retains its structure and optical properties at autoclaving conditions, said second type epoxy being a high temperature grade, more rapidly setting epoxy which retains its structural and optical properties at autoclaving temperature, said third type epoxy being a high temperature, flexible epoxy, said first type epoxy preventing steam from reaching and contaminating the lens during autoclaving, said jacket being preshrunk at autoclaving conditions to minimize jacket shrinkage during autoclaving of the endoscope, a first metal connector at the proximal end of the illumination guide, said connector including a high heat conductivity metal ferule bonded to the light fibers by said second type epoxy, and second metal connector at the proximal end of the image guide.

2. The improvement of claim 1 wherein: said metal ferule of said first metal connector is copper.

3. The improvement of claim 2 wherein: said first and second metal connectors are aluminum.

4. The improvement of claim 3 wherein: said third type epoxy bonds the jacket to the hand piece and to all connectors.

5. The improvement of claim 4 wherein: said first metal connector is bonded to the light fibers by an epoxy selected from said first and second types.

6. The improvement of claim 2 wherein: said third type epoxy bonds the jacket to the hand piece and to all connectors.

7. The improvement of claim 3 wherein: said first metal connector is bonded to the light fibers by an epoxy selected from said first and second types.

8. The improvement of claim 1 wherein: said first and second metal connectors are aluminum.

9. The improvement of claim 8 wherein: said third type epoxy bonds the jacket to the hand piece and to all connectors.

10. The improvement of claim 9 wherein: said first metal connector is bonded to the light fibers by an epoxy selected from said first and second types.

11. The improvement of claim 1 wherein: said third type epoxy bonds the jacket to the hand piece and to all connectors.

12. The improvement of claim 1 wherein: said first metal connector is bonded to the light fibers by an epoxy selected from said first and second types.

* * * * *